United States Patent [19]

Man

[11] Patent Number: Plant 6,321

[45] Date of Patent: Oct. 4, 1988

[54] DISTINCT VARIETY OF BEGONIA PLANT NAMED ROSALIE

[75] Inventor: Jan Man, Lisse, Netherlands

[73] Assignee: Oglevee Associates, Inc., Connellsville, Pa.

[21] Appl. No.: 885,544

[22] Filed: Jul. 14, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new Begonia variety is characterized by its fullness of form and extensive branching. Flowers are brightly colored and clean in appearance. The plant is highly floriferous and the entire plant becomes covered with bloom. The new cultivar has a high tolerance to botrytis and powdery mildew..

1 Drawing Sheet

BACKGROUND OF THE NEW PLANT

The present invention comprises a new and distinct cultivar of *Begonia*×*hiemalis* known by the varietal name of Rosalie. The new cultivar is a selection of a cross between the seed parent Illona and the pollen parent Marja. The cultivar has a serrated leaf like Marja but is much lighter in color. The new cultivar is taller and has a more pleasing form than either parent. The light pink double bloom differs from the apricot bloom of Illona and the red single and double bloom of Marja.

The new cultivar was discovered in April of 1981 at Limaplant b.v. in Lisse, Holland; was first asexually reproduced by cuttings at Limaplant b.v. in Lisse, Holland; and has been repeatedly asexually reproduced by cuttings for Oglevee Associates, Inc. in Connellsville, Pa. It has been found to retain its distinctive characteristics through successive propagations.

The new cultivar is generally characterized by its fullness of form and extensive branching. Flowers are brightly colored and clean in appearance. The plant is highly floriferous and the entire plant becomes covered with bloom. The new cultivar has a high tolerance to botrytis and powdery mildew.

The new cultivar, when grown in a greenhouse in Connellsville, Pa. has a response time of 10 to 11 weeks from a well-rooted cutting to a flowering finished plant in a six inch pot (no pinch).

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out for Oglevee Associates, Inc. in Connellsville, Pa. The plant history was taken on ten week plants blossomed under natural light in a greenhouse and grown under temperature conditions of 62° F. at night and 68° F. during the day. The plants were potted in a peat-lite mix and fertilized with a 100 ppm mixture of 15N-0P-15K. Color readings were taken indoors under 200 footcandles of cool white fluorescent tubes. Color references are to the R.H.S. Colour Chart of The Royal Horticultural Society of London, unless noted differently.

Botanical classification: *Begonia*×*hiemalis.*

Flower:

*Fully expanded.*—4 cm in diameter; side view; semicircle appearance.

*Buds.*—2 cm wide; lower ½; yellow-green group 145D; upper ½: red group 49C; edge: red group 49A. Color shift is gradual. No lines of division.

*Borne.*—Compound dichasium (cyme).

*Stems.*—Peduncles are strong and upright; main peduncle 6 mm in diameter; color yellow-green group 145B.

*Form.*—Semi-double to fully double. Each flower generally has 2 sepals, 7 petals, 7 petaloids (each group may vary±1 structure).

*Permanence.*—Long lasting bloom, generally an individual flower will remain fresh for 2–3 weeks.

Color:

*Tonality from a distance.*—Pastel peach with pink tones. The intensity of the color of the flower decreases with age.

*Front of petals.*—Outer margin and body are characterized by Red Group 49C.

*Base of petal.*—Red Group 29C.

*Reverse of petal.*—Outer margin Red Group 49C. Body: Lightens to include tones of Orange Group 27A and Yellow Green Group 150D.

*Calyx.*—Front of calyx: On mature and fully expanded parts outside margin Red Group 49A which lightens as the center of calyx is approached. Base of calyx Yellow-Green Group 150C. Reverse of calyx: On mature and fully expanded parts outside margins Red Group 49A, which lightens as the center of calyx is approached.

Petals:

*Appearance.*—Oval with color gradient. Outer edge: dark pink→light pink→light orange→light green.

*Arrangement.*—Semi-double to fully double.

*Persistence.*—Family persistence, easily bruised by mechanical injury. Once flowering has begun, it will flower constantly all summer until killed by frost.

*Fragrance.*—None observed.

Reproductive organs: All reproductive organs have modified into petaloids. Anthers, filament, pollen and style could not be observed.

Plant:

*Form.*—Compact, close internodes (1–2 cm apart) upright; good self-support strength, good axillary shoot formation.

*Growth.*—Very vigorous; plant growth can be modifed by changing environmental conditions in which the plant is grown (higher the temperature, the faster and more lush the growth will be).

*Height from soil line.*—20–22 cm in 11 weeks (no pinch).

*Spread.*—34–36 cm in 11 weeks (no pinch).

Foliage:

*Size.*—Depends on how the plant was grown and position on plant; average length of 13 cm and average width of 11 cm, can get as large as length of 18 cm and width of 15 cm.

*Quantity.*—Very abundant.

*Shape.*—Ovate tip with oblique petiole attachment; edge is doubly serrate.

*Top side.*—Green group 137A; shiny and smooth.

*Underside.*—Green group 138B to 138C; veins raised in palmate arrangement.

*Ribs and veins.*—Smooth on top side, raised on lower side, lower side veins only area on leaf where visible tricomes (hairs) appear.

*Rib and vein color.*—Top side: green group 137D; bottom: yellow-green group 146D.

*Margin.*—None.

*Stipules.*—None.

*Texture.*—Top: smooth, shiny and leathery; bottom: matt finish with raised veins.

I claim:

1. A new and distinct variety of Begonia characterized by its fullness of form, extensive branching, flowers brightly colored and clean in appearance, highly floriferous, the entire plant becoming covered with bloom, and high tolerance to botrytis and powdery mildew as herein shown and described and parts therefor.

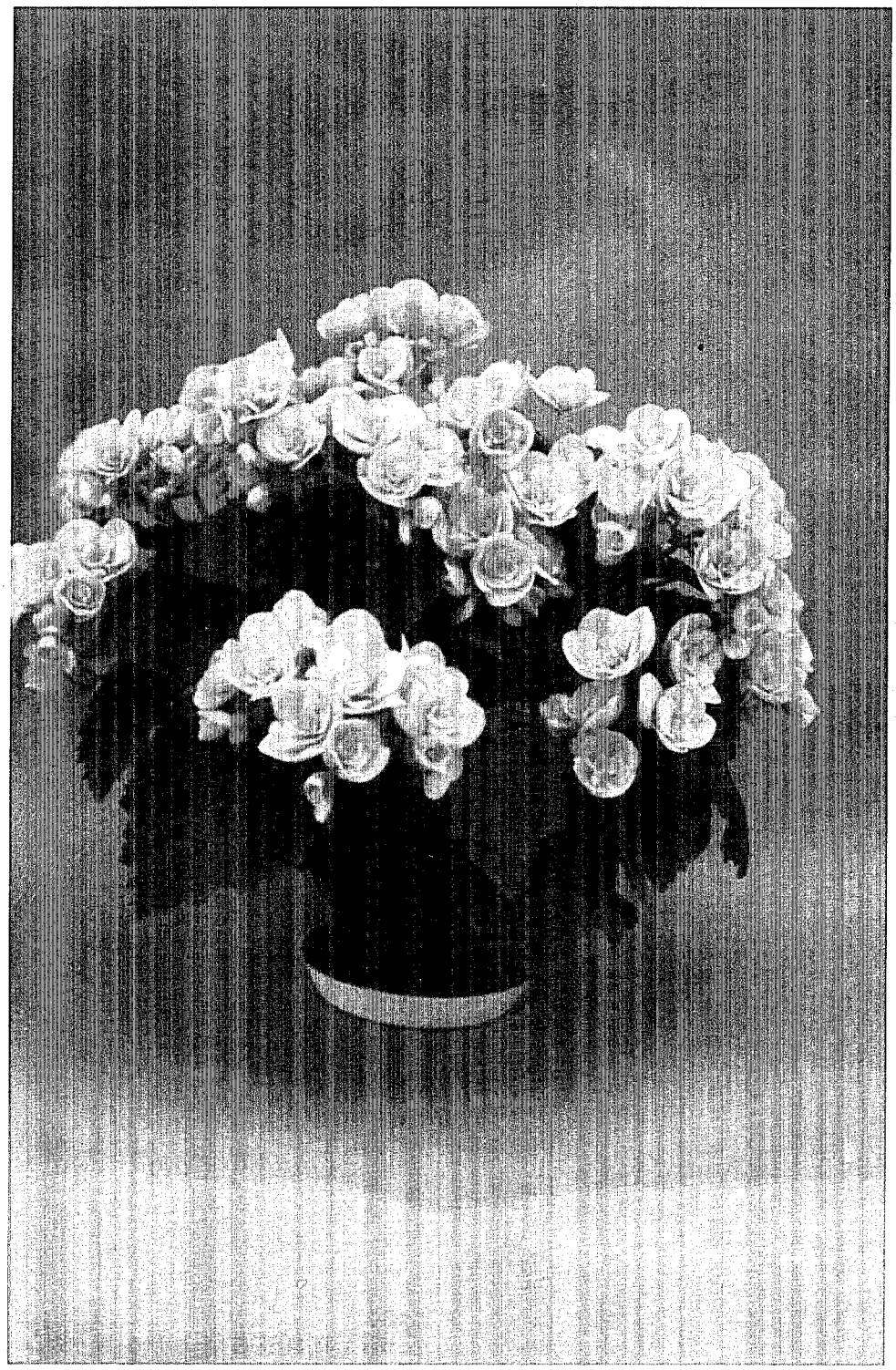

* * * * *